US00PP23224P2

(12) United States Plant Patent
Lichacz

(10) Patent No.: US PP23,224 P2
(45) Date of Patent: Nov. 27, 2012

(54) ***HOSTA* PLANT NAMED 'AUTUMN FROST'**

(50) Latin Name: ***Hosta* hybrid (Tratt.)**
Varietal Denomination: Autumn Frost

(75) Inventor: Susan Lichacz, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 28 days.

(21) Appl. No.: 13/066,786

(22) Filed: Apr. 25, 2011

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt

(57) ABSTRACT

*Hosta* plant named 'Autumn Frost' with cordate leaves having blue-green centers and wide yellow margins that develop into a creamy yellow to cream margins. Flowers are medium lavender on medium-sized plant held attractively above the foliage.

1 Drawing Sheet

Botanical classification: *Hosta* hybrid (Tratt.).
Variety denomination: 'Autumn Frost'.

BACKGROUND OF THE INVENTION

The present invention relates to the new and distinct *Hosta* plant, *Hosta* 'Autumn Frost' discovered by Susan Lichacz at a nursery in Zeeland, Mich., USA in the summer of 2007 as an uninduced whole plant mutation in a tissue cultured crop of *Hosta* 'First Frost' (not patented). The new plant has been successfully asexually propagated both by division and by tissue culture at a nursery in Zeeland, Mich. and in both asexual propagation systems found to be stable and produce identical plants that maintain the unique characteristics of the original plant.

BRIEF SUMMARY OF THE INVENTION

*Hosta* 'Autumn Frost' differs from its parent, 'First Frost', as well as all other *Hostas* known to the applicant. *Hosta* 'First Frost' is a sport from *Hosta* 'Halcyon'. Other sports from 'Halcyon' with light margins include: 'Blue Ivory' U.S. Plant Pat. No. 19,623, 'El Nino' U.S. Plant Pat. No. 14,632, 'Great Escape' U.S. Plant Pat. No. 19,003 and 'Sleeping Beauty' (not patented). *Hosta* 'Autumn Frost' has a wide margin that begins the season yellow and develops into a creamy-yellow to cream. *Hosta* 'El Nino' has a creamy to white-colored margin and is narrower than 'Autumn Frost'. 'Blue Ivory' and 'Great Escape' have wide margins but the color of the margin starts off white to greenish-white then develops into a cream to white and occasionally in high temperatures becomes misted with green. All of the above have similar flower color.

There are over 4,500 cultivars registered with The American *Hosta* Society, which is the International Cultivar Registration Authority for the genus *Hosta* with another similar number of unregistered cultivars. *Hosta* 'Autumn Frost' differs from all these registered and unregistered cultivars known to the inventor in the following combined traits:

1. Plant of medium size with upright to gradually arching foliage.
2. Cordate leaves with blue-green centers and wide yellow margins that develop into a creamy yellow to cream.

3. Numerous flowers of medium lavender held attractively above foliage in mid-summer.

BRIEF DESCRIPTION OF THE DRAWINGS

The photographs of the three-year old plant demonstrate the overall appearance of the near-mature plant, including the unique traits, grown in a partially shaded garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
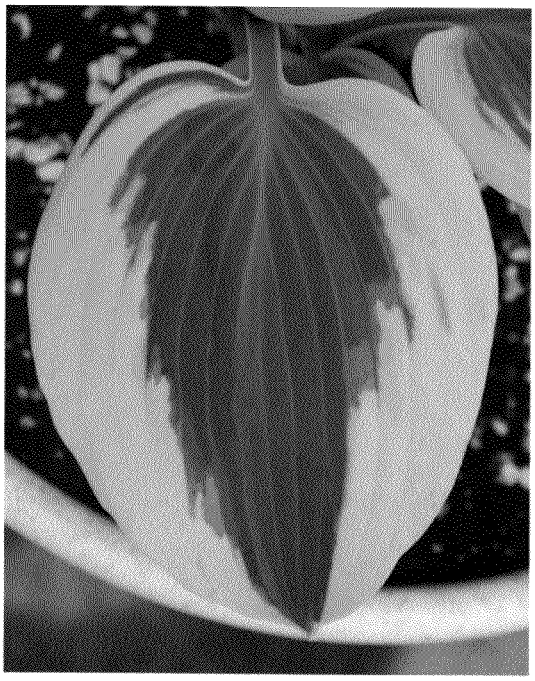
FIG. 1 shows a leaf close-up of a one-year old plant in the early part of the growing season.
Figure 2:
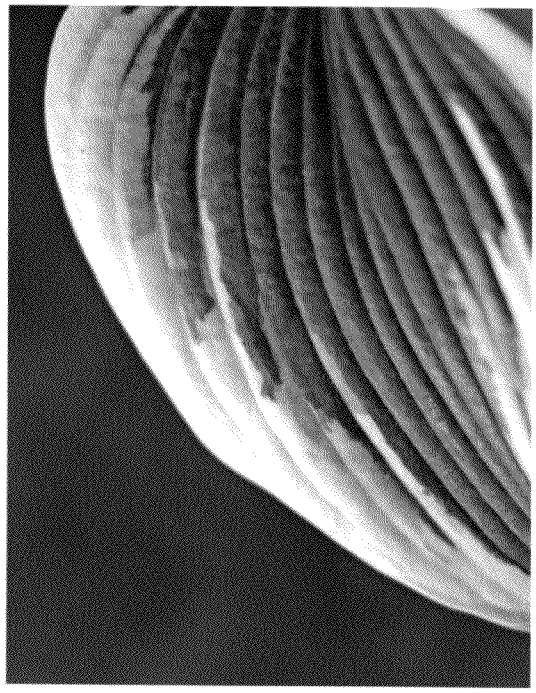
FIG. 2 shows a close-up of the foliage about flowering time, later in the season.
Figure 3:
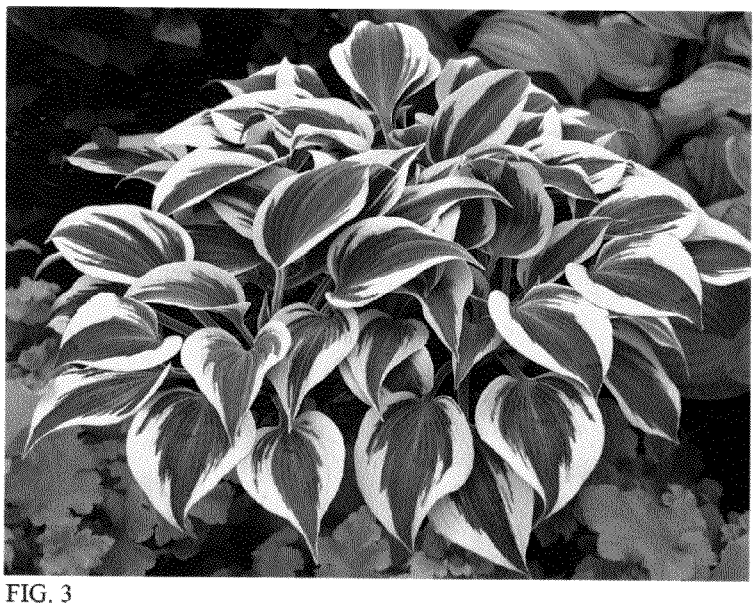
FIG. 3 shows a three-year old plant in a landscape setting about mid season.

The following descriptions and color references are based on the 2001 edition of The Royal Horticultural Society Colour Chart except where common dictionary terms are used. The new plant, *Hosta* 'Autumn Frost', has not been observed under all possible environments. The phenotype may vary slightly with different environmental conditions, such as temperature, light, fertility, moisture and specimen maturity, but without any change in the genotype. The following observations and size descriptions are of a two-year old plant in a trial garden in Zeeland, Mich. with 50% artificial shade, supplemental water and light fertilizer.

Botanical classification: *Hosta* hybrid.

Sport parentage: *Hosta* 'First Frost' (not patented).

Propagation method: By sterile laboratory tissue culture propagation and garden division.

Growth rate: Moderate.

Crop time: Summer growing 10 to 12 weeks to finish in a one-liter container.

Time to initiate roots from tissue culture: About two and a half weeks.

Plant description:

*Plant shape and habit*.—Hardy, long-lived, herbaceous perennial, densely rhizomatous, forming a mounded clump in maturity, with basal rosette leaves; usually bilateral and radially symmetrical.

*Roots*.—Normal, fleshy, lightly branching, cream-colored in normal soil.

*Plant size*.—Foliage height about 50 cm tall; width of plant at the widest point is approximately 72 cm at the widest point just above soil line.

Foliage description:

*Leaf blade*.—Cordate, entire margins, cordate leaf base with acute apex, flat, mostly bilaterally symmetrical, without sinuous or pie-crust margins, with moderately impressed veins; width to length ratio of about 1:1.5; average about 15 cm long and 10 cm wide; 10 to 11 pairs of major parallel veins and one main center vein; glabrous; adaxial (top) surface glaucous becoming dull matte-surfaced late in growing season, abaxial surface (bottom) highly glaucous remaining throughout growing season; margin variegation portion increasing with age from ⅓ to nearly ½ total leaf width.

*Blade color*.—Early season as emerging adaxial (top) center nearest RHS N138A, adaxial margin nearest RHSN144A, intermediate colors of RHS 145A, nearest RHS 138D and nearest RHS 148D in small irregular patches between the margin and center; early season as emerging abaxial (bottom) center nearest RHS N138C, abaxial margin more yellow than RHS N144B and more green than RHS 1B, intermediate colors of nearest RHS 145B and nearest RHS 147D in very small irregular patches between the margin and center; mid-season and later adaxial center nearest RHS 136A, creamy margin nearest RHS 10D and small irregular intermediate patches of nearest RHS N138D, nearest RHS N144C and nearest RHS 192C; mid-season and later abaxial center nearest RHS N138C, creamy margins nearest RHS 10D and small irregular intermediate patches of nearest RHS 145C and nearest RHS 154D.

*Veins*.—10 to 11 pairs of major parallel veins, with one major center vein.

*Vein color*.—On early season adaxial center nearest RHS 138C and nearest RHS 160C in the margin; abaxial margin and center the same color as the surrounding leaf tissue; mid season and later nearest the glaucous covering remains longer in the veins maintaining a lighter color in the center of nearest RHS 138D and on the margin nearest RHS 157B; adaxial side the same color as the surrounding tissue on both margin and center.

*Petioles*.—Concavo-convex, glabrous, glaucous, upright to arching; 38 to 42 cm long and about 1.3 cm wide measured at 3 cm above soil line.

*Petiole color*.—Margins of petiole same as the respective adaxial blade margins in early season and mid to late season; adaxial and abaxial center between RHS 139C and RHS 139B in the distal portion and developing a fine speckling of nearest RHS N186C in the proximal portion of both surfaces, with the speckling more concentrated closer to the base.

Flower description:

*Buds*.—Clavate, bluntly acute to rounded apex with longer thin base; one day prior to opening about 4.5 cm long, and 1.5 cm wide at the broadest portion; nearest RHS N81A on exposed margin of tepal and near base and lighter (more white) than RHS 851D at middle and a 1.0 to 2.0 mm green apex nearest RHS 138B.

*Flowers*.—16 to 28 per scape; each subtended by bract; funnelform; about 5.5 cm wide and 7.5 cm long, (distal flowers slightly smaller); remain open for a normal period, usually one to two days on or cut from plant; scapes remain effective from mid-July into mid-July in Zeeland, Mich.; no detectable fragrance.

*Tepals*.—Two sets of three fused at the basal two thirds; acute apex; margins entire; glabrous, approximately 5.0 cm long and 1.5 cm wide.

*Tepal color*.—Abaxial outer tepal set color nearest RHS 85D on the center middle and between RHS 85D and RHS 85C on the edge or of the outer tepals with the 1 mm apex nearest RHS 137B; abaxial inner tepal lighter (more white) than RHS 85D; adaxial outer tepals center middle portion nearest RHS N82D with three veins of nearest RHS N82B and edge lighter (more white) than RHS 85D; adaxial inner tepals nearest N82C with margins of lighter (more white) than RHS 85D and a clear edge about 1.0 mm wide.

*Pedicel*.—Rounded, slightly curved, glaucous, glabrous; about 7 mm long, 3 mm diameter; nearest RHS 138C.

*Peduncle*.—Cylindrical, glaucous, glabrous, unbranched; usually one per division, slightly arching to about 60 degrees from horizontal; about 4 mm diameter at base, about 20 cm tall; nearest RHS 139C.

*Gynoecium*.—Single. Style: about 5.0 cm long, 1 mm diameter, slightly curled upward at distal ⅓; lighter (more white) than RHS 11D the whole length. Stigma: rounded, 1 mm to 2 mm in diameter, lighter than RHS 115D. Ovary: oval, about 6 mm long and 3 mm diameter; between RHS 145A and RHS 145B.

*Androecium*.—Six. Filaments: six, about 1.0 mm in diameter and 4.8 cm long, shorter than gynoecium; with slight curve upward the proximal ⅓; lighter than RHS 11D throughout. Anthers: oblong; attached midpoint lengthwise; dehiscing along the center longitudinal axis; about 3 mm long and 1 mm wide, color nearest RHS 176A prior to anthesis and nearest RHS N186A after anthesis. Pollen: elliptical, less than 0.1 mm long, nearest RHS 21A.

*Bracts*.—Subtending each flower, lanceolate, entire, glaucous, glabrous, concavo-convex, widest at middle and tapering to acute apex, sessile, clasping about ½ peduncle; protruding upward about 20 degree angle away from scape at time of flower opening; with lowest about 2.5 cm long and 1.4 cm wide before first flower, progressively decreasing in both length and width; drying as flowers open.

*Bract color*.—Abaxial 1.0 to 2.0 mm wide margins between RHS 157A and RHS 156A with tinting of nearest RHS 183C; central abaxial portion between RHS 137A and RHS 137B; on top and bottom surfaces lighter than RHS 145D with outer portion nearest RHS 139C and a thin margin about 1 mm wide of nearest RHS 139D; adaxial margins nearest RHS 145C and central portion nearest RHS 138B.

Fruit: Has not been observed.

Seeds: Have not been observed.

Disease resistance: Disease or pest resistance beyond that common to *Hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *Hostas*.

I claim:

1. A new and distinct ornamental *Hosta* plant named 'Autumn Frost' as herein described and illustrated, with cordate leaves having blue-green centers and wide yellow margins that develop into a creamy yellow to cream, medium lavender flowers on medium-sized plant, suitable as a potted plant, for the garden, and for cut flower or leaf arrangements.

* * * * *